United States Patent [19]

Faulhaber

[11] Patent Number: 4,538,915
[45] Date of Patent: Sep. 3, 1985

[54] WEB INSPECTION SYSTEM HAVING A PRODUCT CHARACTERISTIC SIGNAL NORMALIZING NETWORK

[75] Inventor: Mark E. Faulhaber, Wilmington, Del.

[73] Assignee: E. I. Du Pont de Nemours and Company, Wilmington, Del.

[21] Appl. No.: 333,783

[22] Filed: Dec. 23, 1981

[51] Int. Cl.³ ............................................. G01N 21/32
[52] U.S. Cl. ..................................... 356/431; 250/563
[58] Field of Search .................... 356/429, 430, 431; 250/563, 572; 350/6.8

[56] References Cited

U.S. PATENT DOCUMENTS

| | | | |
|---|---|---|---|
| 2,864,277 | 12/1958 | Eichorn | 356/431 |
| 3,646,331 | 2/1972 | Lord | 235/151.3 |
| 3,843,890 | 10/1974 | Anthony et al. | 250/563 |
| 3,849,004 | 11/1974 | Cofek | 250/563 |
| 3,919,473 | 11/1975 | Cotter | 178/7.2 |
| 3,920,970 | 11/1975 | Slaker | 235/151.3 |
| 3,934,136 | 1/1976 | Schoon | 250/214 R |
| 4,005,281 | 1/1977 | Faulhaber et al. | 356/239 |
| 4,048,510 | 9/1977 | Clarke et al. | 250/563 |
| 4,054,377 | 10/1977 | Gibson | 356/199 |
| 4,155,012 | 5/1979 | Clark et al. | 250/572 |
| 4,297,587 | 10/1981 | Baker | 250/563 |
| 4,420,742 | 12/1983 | Tadauchi et al. | 340/347 AD |

Primary Examiner—R. A. Rosenberger
Attorney, Agent, or Firm—George M. Medwick

[57] ABSTRACT

An inspection system of the type having a rotating multifaceted mirror and a radiation collecting arrangement is characterized by a network in which the signal representative of the web being inspected is compensated for deviations superimposed on that signal due to variations in the reflectivity among the various mirror facets and normalized for variations in the optical efficiency of the radiation collecting arrangement.

15 Claims, 6 Drawing Figures

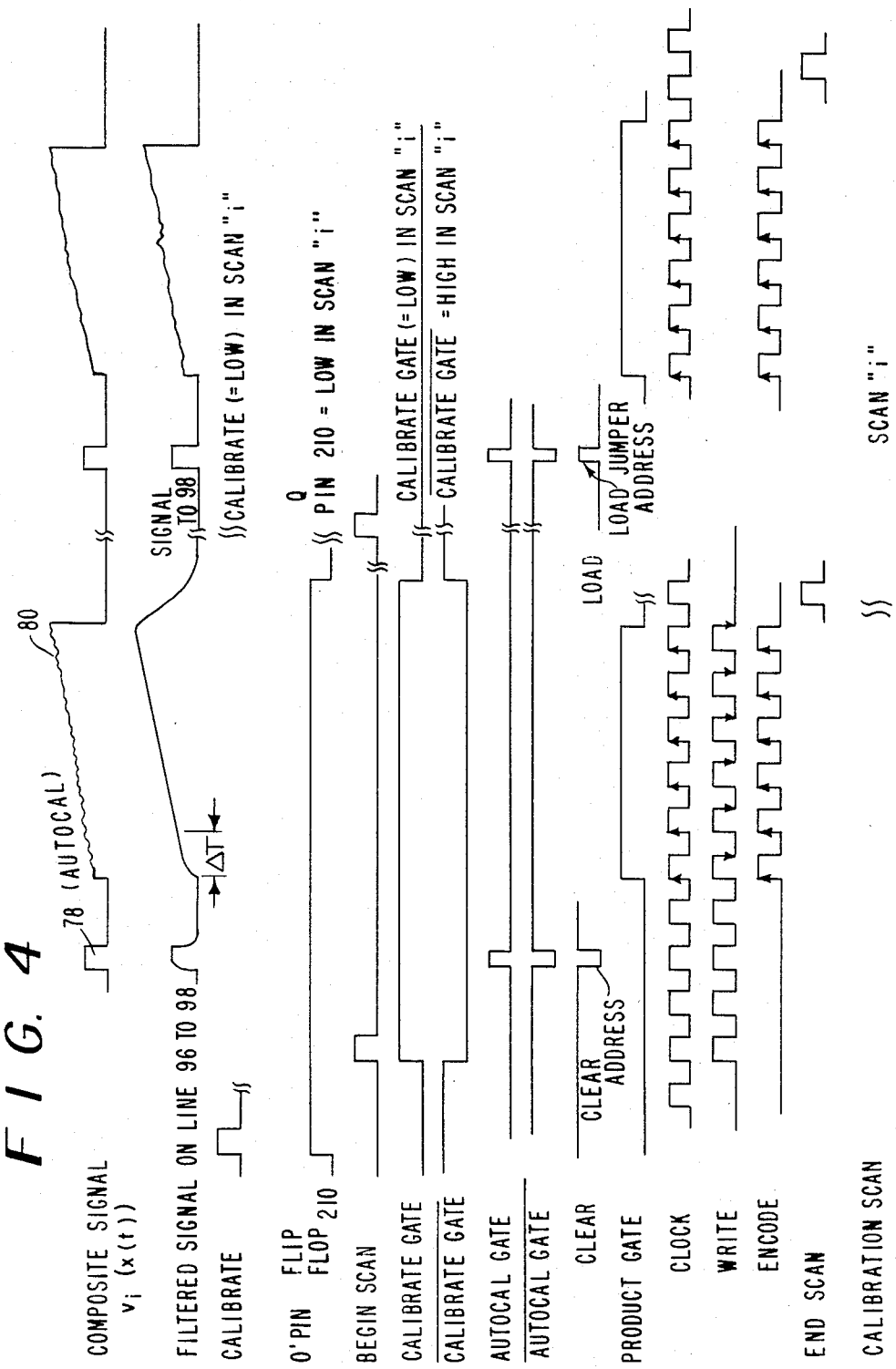

WEB INSPECTION SYSTEM HAVING A PRODUCT CHARACTERISTIC SIGNAL NORMALIZING NETWORK

BACKGROUND OF THE INVENTION

This invention relates to a web material inspection system of the type that utilizes a rotating multifaceted mirror to direct a scanning beam of radiation towards a radiation collecting arrangement suitably disposed with respect to the web. In particular, the invention relates to an inspection system in which the signal representative of the web being inspected is compensated for deviations superimposed on that signal due to variations in the reflectivity among the various mirror facets and normalized for variations in the optical efficiency of the radiation collecting arrangement.

Opto-electrical web inspection systems using the calibrated flying spot scan technique to automatically inspect web material, such as webs of X-ray film or fabric, are known. Exemplary of such an apparatus is that disclosed in U.S. Pat. No. 3,843,890 issued to Anthony, Jr. et al. and assigned to the assignee of the present invention. The web inspection apparatus generally comprises a source of scanning radiation, means for generating a beam of radiation and for traversing the beam in a scan across the web, and a radiation collecting arrangement positioned with respect to the web and responsive to the radiation either reflected from or transmitted through the web for generating an electrical signal representing a predetermined physical property thereof. The radiation source is typically a laser. The beam of collimated light from the laser is directed toward the web by a multifaceted rotating mirror disposed within a scanning and focusing optical assembly. The radiation beam appears as a spot traversing the web in a predetermined scan direction. The radiation collecting arrangement, such as a tapered light-conducting rod, collects the radiation reflected by or transmitted through the web, as the case may be, and directs that radiation to a detector. The detector, such as a photomultiplier tube, generates an electrical signal representing a predetermined physical property of the portion of the product web scanned by the radiation beam.

The electrical signal representative of any one scan across the product web is typically represented by a voltage pedestal signal output from the photomultiplier tube. The voltage pedestal signal for a given scan i may be expressed mathematically as a function $v_i(x(t))$ as set forth in Equation (1), $$V_i(x(t)) = K_i(x(t)) \cdot P_i(x(t)) \tag{1}$$

where $x(t)$ is the distance traversed across the web measured from an initial position, $x_o$, at the start of each scan across the product web as a function of time t, $P_i(x(t))$ is the electrical signal representative of a predetermined physical property of the portion of the web scanned by the radiation beam at time t during scan i. This term is also referred to as the product characteristic, and $K_i(x(t))$ is an attenuation function, valid for scan i, which is mathematically defined as $$K_i(x(t)) = I_o(t) \cdot R_{iF} \cdot G_o(t) \cdot G_e(t) \cdot E_o(x) \tag{2}$$

where $I_o(t)$ is the radiation source intensity, $R_{iF}$ is the reflectivity of a mirror facet on the i-th scan, where $i_F = (i$ MODULO $F)$, i is the scan number $(i=0,1,2...)$ and F is the number of facets, $G_o(t)$ is the optical system gain, $G_e(t)$ is the electrical system gain, and $E_o(x)$ is the optical efficiency of the radiation collecting system.

As seen from Equation (1) the voltage pedestal signal $v_i(x(t))$ output from the photomultiplier tube is a function of both position (with respect to the web) and time. The product characteristic component $P_i(x(t))$ of the voltage pedestal is that portion of the voltage pedestal due to reflectivity or transmissivity of the scanning radiation by the product web. The voltage pedestal signal $vi(x(t))$ is also functionally related to an attenuation function $K_i(x(t))$ which is itself a function of position across the web and time.

Examples of causes for variations in the radiation source intensity $I_o(t)$ may include power supply voltage level changes and aging of the laser optics or laser components. Optical system gain variations $G_o(t)$ may originate as the result of photomultiplier tube aging, dust on the radiation collecting arrangement or on the entrance and exit ports of the optical scanning and focusing assembly. Electrical system gain variations $G_e(t)$ may derive from changes in electronic component characteristics in various of the electronic stages. Variations in these parameters generally occur in the same time scale and may be correctable utilizing automatic gain control circuitry. As a consequence the effect of these parameters on the voltage pedestal signal $v_i(x(t))$ may be minimized or eliminated.

On the other hand, scanning mirror reflectivity variations $R_{iF}$ occur over a much shorter time since they may originate as a result of uneven reflective properties among various of the F facets of a rapidly rotating multifaceted mirror. Although the reflectivity across the span of any one facet is relatively constant, variations in reflectivity can occur from facet to facet. Haze and dust are generally not included as causes of mirror reflectivity variations because it is assumed that the buildup of haze and dust on each of the facets in the multifaceted rotating mirror is relatively uniform. The optical efficiency of the radiation collecting arrangement $E_o(x)$ is a function of the distance from the detector at which the reflected or transmitted radiation impinges upon the collecting rod and is invariant with time.

In order to make the voltage pedestal signal $v_i(x(t))$ output from the photomultiplier tube dependent only upon the product characteristic $P_i(x(t))$ of the web being inspected it is necessary to compensate in some manner for both the effects of variations in mirror reflectivity among the mirror facets and for the variations in the optical efficiency of the radiation collecting arrangement.

SUMMARY OF THE INVENTION

In accordance with this invention a flying spot scanning beam inspection system is provided with a product signal normalizing network which compensates the voltage pedestal $v_i(x(t))$ for variations caused by differences in reflectivity among mirror facets and which normalizes the voltage pedestal to account for the spatial variations in optical efficiency of the radiation collecting arrangement. In response to a calibrate initiated by an operator the product web is scanned once during a calibration period and the result applied to a rationing analog-to-digital converter to generate a product characteristic calibration signal $P_c(x(t))$ which is independent of the reflectivity of the particular mirror facet used during the calibration scan. During subsequent analytical scans, e.g., the i-th scan, the product characteristic calibration signal $P_c(x(t))$ is scaled in accordance with the reflectivity of the particular mirror facet $R_{mF}$ used during that scan. The scaled signal is applied to the rationing analog-to-digital converter together with the product characteristic signal $P_i(x(t))$ for the i-th scan to generate a normalized product characteristic signal $P_n(x(t))$. The normalized product characteristic signal $P_n(x(t))$ is not only compensated for the reflectivity of the facet used during the i-th scan but is also normalized to account for the variations in optical efficiency of the radiation collecting arrangement.

The product characteristic calibration signal $P_c(x(t))$ is generated by first sampling the signal output from the radiation collecting arrangement during a segment of the calibration scan in which the radiation beam does not impinge upon the product web. This signal magnitude $R_{iF}$, which is a function of the reflectivity of the mirror facet used during the calibration scan, is held and applied as a reference input to the rationing analog-to-digital converter. Throughout the succeeding segment of the calibration scan during which voltage pedestal signal is generated by the photomultiplier tube, the voltage pedestal signal is divided by the sampled signal representing mirror reflectivity to produce the product characteristic calibration signal $P_c(x(t))$. The product characteristic calibration signal $P_c(x(t))$ may be stored in a suitable memory device and recalled for use during subsequent scans. During a portion of each subsequent scan in which the radiation beam does not impinge upon the product web the signal output from the radiation collecting arrangement is sampled. This sampled signal is functionally related to the reflectivity of the mirror facet used during that scan and is applied to the stored product characteristic calibration signal using a multiplying digital-to-analog converter to scale accordingly the product characteristic calibration signal.

BRIEF DESCRIPTION OF THE DRAWINGS

The invention may be more fully understood from the following detailed description thereof taken in connection with the accompanying drawings which form a part of this application and in which:

FIG. 4 is a timing diagram for the signals generated and utilized in the network shown in FIGS. 2 and 3.

DISCLOSURE OF THE INVENTION

Figure 1:
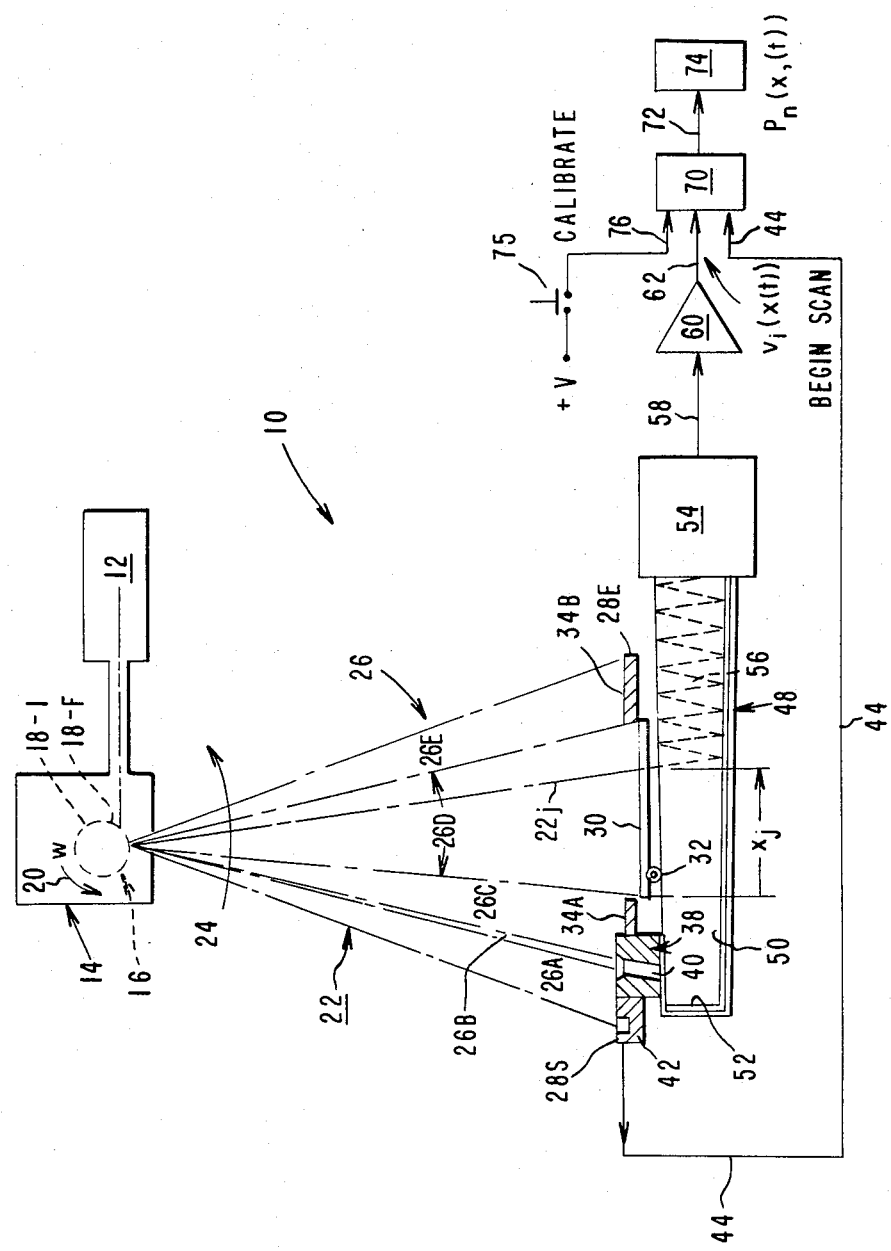
FIG. 1 is a schematic plan view of a flying spot web inspection apparatus with which the instant invention is utilized.

Throughout the following detailed description similar reference numerals refer to similar elements in all figures of the drawings.

With reference to FIG. 1, shown is a plan view of a flying spot web inspection apparatus generally indicated by reference character 10 with which the product characteristic signal normalizing network 70 in accordance with this invention (FIGS. 2 through 4) may be utilized. The inspection apparatus 10 includes a source 12 of radiation such as that provided by a helium neon laser. Of course, other suitable radiation sources may be used. The radiation source 12 is connected to a scanner and focusing optics assembly 14 within which is disposed a multifaceted rotating mirror 16. The mirror 16 contains an array of facets 18-1 through 18-F which are arranged to be driven in a direction 20 at a predetermined angular velocity w by a suitable motor drive (not shown), all in accordance with established teachings in the art.

As the mirror 16 is rotated each of the facets 18 thereon is arranged to direct a focused beam 22 of radiation in a scanning direction indicated by reference arrow 24 at a speed functionally related to the angular velocity w across a scan path 26 defined between a start-scan position 28S and an end-scan position 28E. The scan path 26 across which the radiation beam 22 traverses may be subdivided into a plurality of scan segments 26A through 26E for purposes which become clearer herein. The scan path 26 lies substantially transversely of the direction in which a web 30 of material to be inspected is conveyed. The direction of travel of the web 30 is out of the plane of FIG. 1, as indicated by the reference arrow 32. The web 30 is constrained between suitable rollers (not shown) and passes between masks 34A and 34B. Disposed adjacent to the mask 34A at a point upstream in the beam scan path 26 (in a direction counter to the direction of the arrow 24) is an autocalibration filter assembly 38. The autocalibration filter assembly 38 includes an aperture 40 provided for a purpose discussed herein. The generation and function of the autocalibration signal (AUTOCAL) is described in full detail in U.S. Pat. No. 3,843,890. Next adjacent in an upstream direction to the filter assembly 38 is a detector element 42, such as a silicon solar cell. The detector 42 is adapted to respond to the impingement of the beam 22 thereon to generate a beginning of scan pulse signal (BEGIN SCAN, FIG. 4) carried by a line 44 to the product characteristic signal normalizing network 70 discussed herein in connection with FIGS. 2 through 4.

A radiation collecting arrangement 48 such as a tapered light conducting rod collector is disposed behind the web 30 opposite to the scanning and focusing optics assembly 14. The radiation collecting arrangement 48 is provided with a reflecting stripe 50 disposed along one surface thereof and has a reflecting surface 52 disposed adjacent to one end thereof. Light entering into the radiation collecting arrangement 48 is reflected by the surface 52 or the strip 50 (as the case may be) and is directed thereby toward a detector element 54 such as a photomultiplier tube. As illustrated by the reflective path 56 traced for a beam 22-j which enters the collecting arrangement 48 at a point $x_j$ (measured in the direction of scan 24 from the beginning of the segment 26D) and at a time $t_j$ (measured from the beginning of the segment 26D), light entering the arrangement 48 is collected and directed toward the photomultiplier tube detector 54. The voltage signal $v_i(x(t))$ output of the photomultiplier tube 54 during any scan i across the web 30 is applied over a line 58 to a preamplifier element 60. The amplified output signal $v_i(x(t))$ from the amplifier element 60 is carried by a cable 62 to the product characteristic normalizing network 70. The output of the normalizing network 70 is the normalized product characteristic signal $P_n(x(t))$ which is applied over a line 72 to a suitable product classification network 74 where signals representative of the acceptability of the scanned product may be generated.

A calibration switch 75 is disposed in a location accessible to the operator of the inspection apparatus 10. When the switch 75 is actuated a calibration signal (CALIBRATE, FIG. 4) is applied on the line 76 to the product characteristic signal normalizing network 70.

As the beam 22 moves across the scan path 26 light reaches the radiation collecting arrangement only during the scan segments 26B and 26D. The voltage pedestal signal $v_i(x(t))$ output on the line 62 from the preamplifier element 60 is a composite signal formed of two components. The first component 78 (AUTOCAL, FIG. 4) is generated when the beam 22 scans across the scan segment 26B and enters the collecting arrangement 48 through the aperture 40 in the filter assembly 38. The amplitude of this signal is representative of the reflectivity $R_{iF}$ of the particular mirror facet 18 used during that particular scan. The second component 80 (FIG. 4) of the signal $v_i(x(t))$ is the product web voltage signal generated as the beam scans across the product web 30 in the scan segment 26D. Assuming appropriate gain control circuitry is provided in the preamplifier 60 to eliminate or minimize the time varying parameters $G_e(t)$, $G_o(t)$ and $I_o(t)$, the second component 80 (the product web voltage signal) is functionally related to the reflectivity of the mirror $R_{iF}$, the optical efficiency $E_o(x)$ of the collecting arrangement, and the characteristic of the product itself.

As discussed earlier, variations in the reflectivity produced by each facet 18 of the multifaceted mirror 16 as well as the optical characteristic of the radiation collecting arrangement 48 prevent the product web voltage signal for the i-th scan $P_i(x(t))$ carried on the line 58 from being an indication of only the properties of the web 28 under test. In accordance with this invention, the product web voltage pedestal component of the signal $v_i(x(t))$ applied to the network 70 is compensated for variations caused by differences in mirror reflectivity among mirror facets and is normalized to a signal representative of acceptable product to eliminate the effects of the nonuniform optical efficiency of the collecting arrangement.

It should be appreciated that although the foregoing description of the flying spot web inspection apparatus 10 illustrates the physical configuration and relationship of the above-described elements for use in a transmissive mode inspection of the product web 30, the product characteristic signal normalizing network 70 in accordance with this invention may be used with equal facility in conjunction with the flying spot inspection apparatus using reflection or other modes of product scanning.

Figure 2:
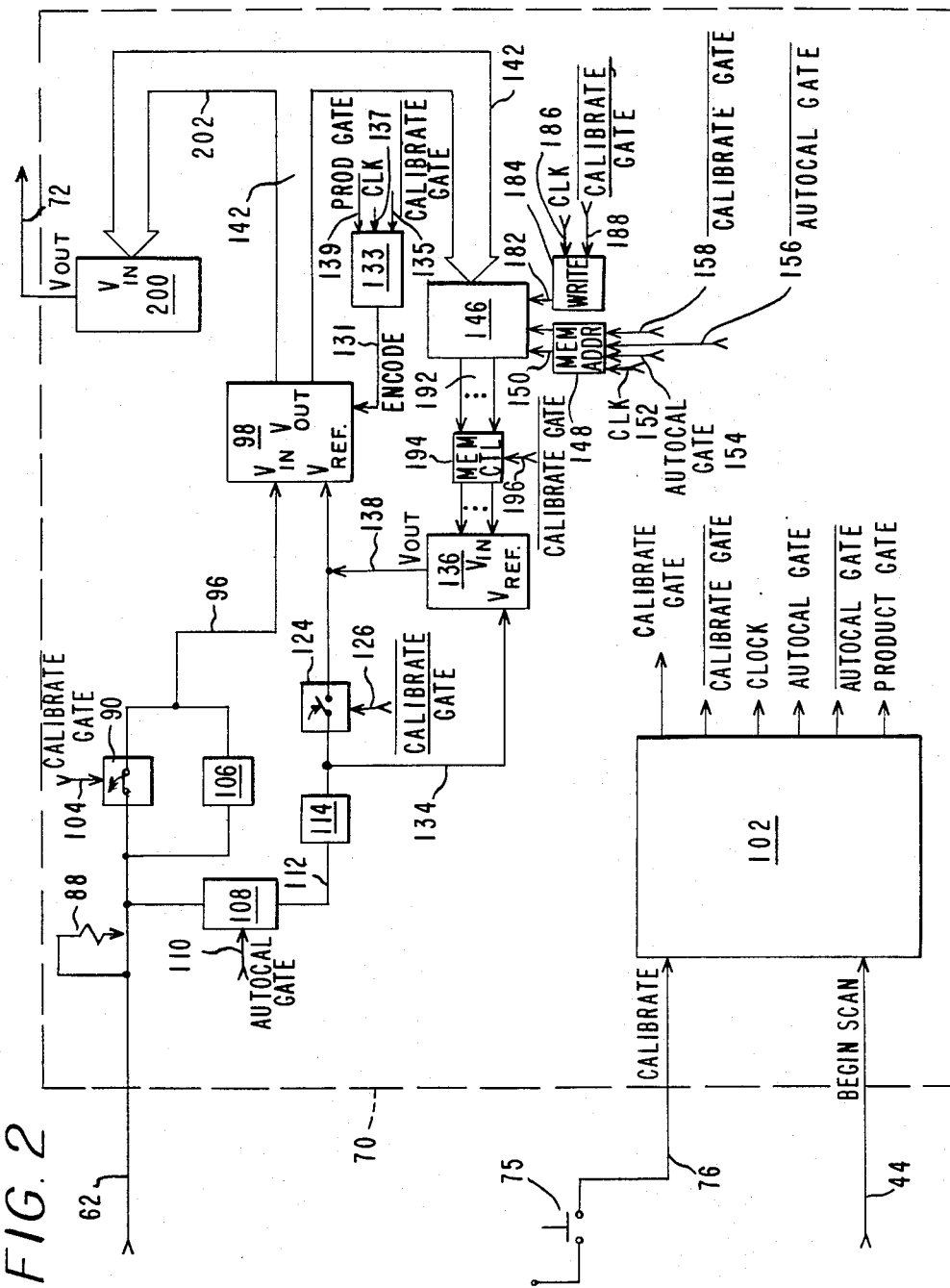
FIG. 2 is a generalized block diagram of the product characteristic signal normalizing network in accordance with the instant invention.
Figure 3A:
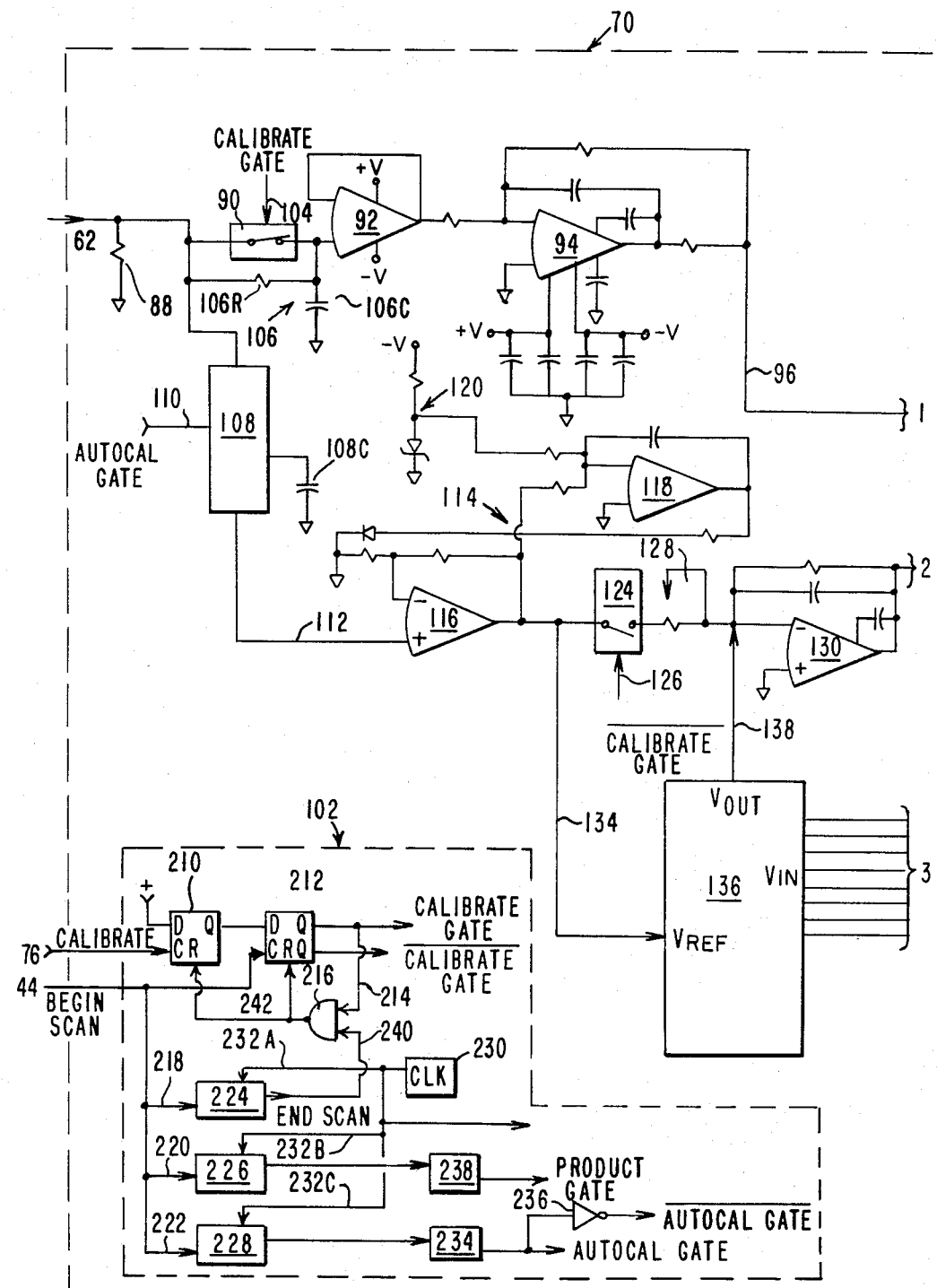
FIGS. 3A, 3B and 3C are more detailed schematic diagrams of the product characteristic signal normalizing network in accordance with the instant invention.
Figure 3B:
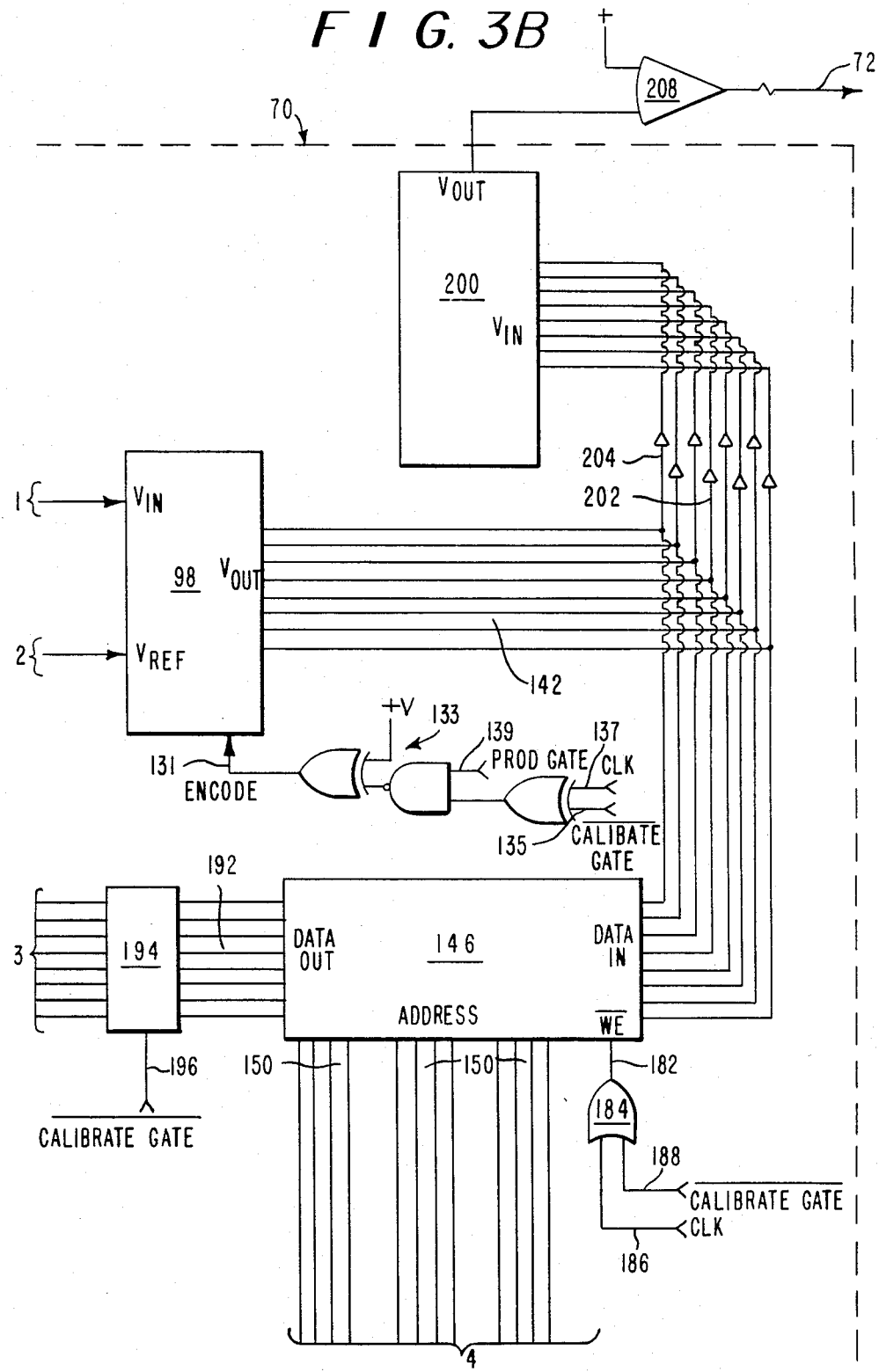
Figure 3C:
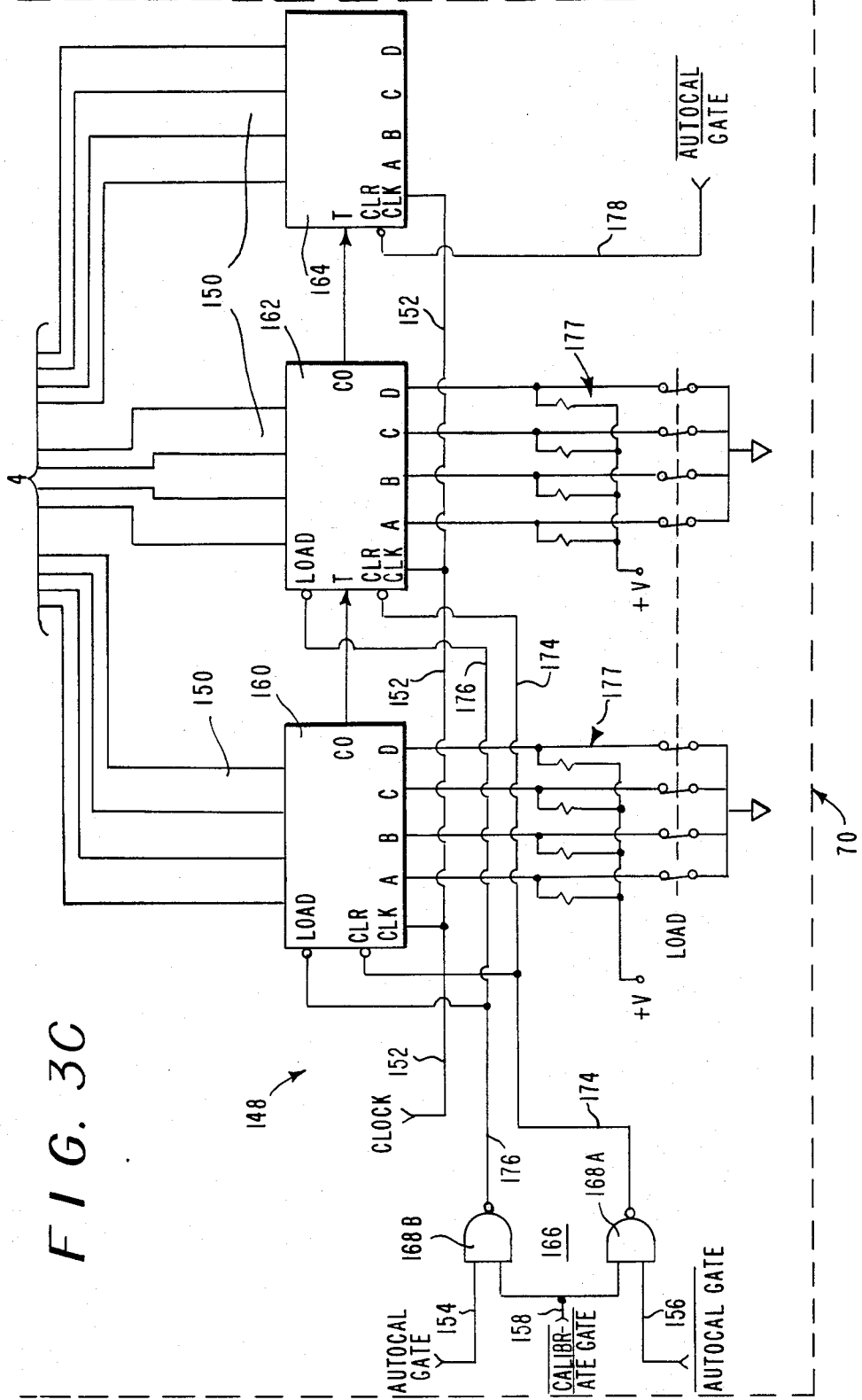

With reference to FIGS. 2 and 3, shown is a generalized block diagram (FIG. 2) and a detailed schematic diagram (FIGS. 3A, 3B and 3C) of the product characteristic signal normalizing network 70 embodying the teachings of the instant invention. The composite voltage pedestal signal for the i-th scan $v_i(x(t))$ (formed of the AUTOCAL pulse 78 and the product web voltage signal 80, FIG. 4) is applied to the normalizing network 70 over the line 62 terminated by a resistor 88 matching the characteristic impedance of the line 62. The composite voltage pedestal is applied through a normally closed. switch 90, through an amplifier 92 and an inverter 94 (FIG. 3A) on a line 96 to the input terminal $V_{in}$ of a ratioing analog-to-digital converter 98. Suitable for use as the ratioing analog-to-digital converter 98 is a device manufactured by TRW, Inc. of Cleveland, Ohio and sold under model number TDC 1007J. The amplifiers 92 and 94 respectively provide signal buffering and inversion to condition the signal to a level and polarity compatible with the ratioing analog-to-digital converter 98. Suitable for use as the amplifier 92 is a device sold by Burr-Brown Inc. under model number 3550 while the amplifier 94 may be realized by a device sold by the same manufacturer under model number 3554.

The state of the switch 90 is controlled by a signal CALIBRATE GATE generated from a control network generally indicated by reference character 102 over a line 104. A solid state switch such as that manufactured by Siliconix Inc. and sold under model number DG200 may be used to implement the switch 90. When the switch 90 is opened under the control of the CALIBRATE GATE signal (FIG. 4) on the line 104, the composite voltage pedestal signal is constrained to pass through a low pass filter network 106 formed from a resistor 106R and a 0.001 microfarad capacitor 106C.

A sample and hold network 108 is connected to the input line 62. The network 108 is under the control of a control signal AUTOCAL GATE (FIG. 4) present on a line 110 from the control network 102. The output of the sample and hold network 108 is held by a one-thousand picofarad capacitor 108C (FIG. 3A) and is applied over a line 112 through an automatic gain control network generally indicated by reference character 114 formed of amplifiers 116 and 118 (FIG. 3A). The automatic gain control network 114 fixes the average output of the amplifier 116 to a selected level. Suitable for use as the sample and hold network is a device sold by Burr-Brown, Inc. under model number SHC85. The automatic gain control network may be configured from amplifers sold by Texas Instruments, Inc. under model number TL087C.

The sampled signal (after appropriate gain control as discussed above) is connected to the reference input terminal $V_{ref}$ of the ratioing analog-to-digital converter 98 through a normally open solid state switch 124. The sampled signal is applied to the converter 98 when the switch 124 is closed by the signal CALIBRATE GATE-NOT generated by the control network 102 on a line 126. The signal passed by the switch 124 is scaled by a potentiometer 128 and inverted by an amplifier 130 (FIG. 3A) similar to the amplifier 94.

However, in the normal case the switch 124 is open and the output of the sample and hold network 108 is applied over a line 134 to the reference input of a multiplying digital-to-analog converter 136.

The analog signal output from the converter 136 is applied (through the inverter 130, FIG. 3A) to the reference input of the ratioing analog-to-digital converter 98 over a line 138. Suitable for use as the multiplying digital-to-analog converter is a device manufactured by Hybrid Systems and sold under model number 390D-10WB. Alternatively, the multiplying digital-to-analog converter 136 may be realized using a device sold by TRW, Inc. under model number TDC-1016J.

Conversion of the analog signal applied to the input terminal of the converter 98 is enabled by an ENCODE signal (FIG. 4) output on a line 131 from an encode enable logic network 133. The network 133 is shown in detail in FIG. 3B. The encode enable network 133 is responsive to the CALIBRATE GATE-NOT signal, a CLOCK signal and a PRODUCT GATE signal respectively input on lines 135, 137 and 139 from the control network 102. As discussed hereinafter, at appropriate times the ENCODE signal is applied to the converter 98 on the line 131 to enable the conversion of analog data present at the input terminal on the line 96 to an eight-bit digital equivalent.

The digitized data on the output terminals of the converter 98 is applied over an eight bit bus 142 to the input terminals of a random access memory 146. The memory may be configured from 4K×1 RAMs manufactured by Fairchild Semiconductor and sold under model number 93471 connected in a bit-slice configuration. Alternately, devices sold by Intel Corp. under model number 2147-3 may be used. Memory addressing for the memory 146 is controlled by a memory address control arrangement generally indicated by reference character 148 which generates appropriate address signals on address lines 150 in response to control signals CLOCK, AUTOCAL GATE, AUTOCAL GATE-NOT and CALIBRATE GATE-NOT applied from the control network 102 on the lines 152, 154, 156 and 158, respectively.

The memory address control network 148 includes an array of cascaded counters 160, 162 and 164 (FIG. 3C) such as those manufactured and sold by Texas Instruments, Inc. under model number SN74LS161. An address advance logic network 166 (FIG. 3C) configured from gates 168A and 168B is arranged to either clear the counters 160 and 162 over a line 174 (CLEAR, FIG. 4) or to enable the counters 160 and 162 on a line 176 (LOAD, FIG. 4) to load the counters with a preset jumpered count derived from a resistor network 177 for a purpose discussed herein. The loading of the preset count into the counters 160 and 162 occurs under the control of the LOAD signal. The counter 164 is cleared by the AUTOCAL GATE-NOT signal on a line 178. The writing of data into the memory 146 is controlled by a WRITE signal (FIG. 4) on a line 182 generated from a write enable control network 184 in response to the CLOCK and CALIBRATE GATE-NOT signals applied thereto over lines 186 and 188, respectively.

The output lines 192 from the memory 146 are connected to the inputs of the multiplying digital-to-analog converter 136 through a memory output gate control network 194. The network 194 is enabled to gate output signals read from the memory 146 by the CALIBRATE GATE-NOT signal applied to the network 194 on a line 196. The network 194 may be eliminated if a multiplying digital-to-analog converter sold by TRW, Inc. under model number TDC-1016J is used.

The output bus 142 from the analog-to-digital converter 98 is connected to the inputs of a digital-to-analog converter 200 by an output bus 202. Suitable for use as the converter 200 is a device sold by Hybrid Systems under model number 390D-10WB. Alternatively, the digital-to-analog converter 200 may be a device sold by TRW, Inc. under model number TDC-1016J. An array of buffers 204 (FIG. 3B) is connected in the output bus 202. Suitable for use as the buffers 204 are devices made by Texas Instruments, Inc. and sold under model number SN74126. The output of the digital-to-analog converter 200 is applied to an amplifier 208 (FIG. 3B), the output of which is connected to the line 72.

The control network 102 (FIG. 3A) is responsive to the signal BEGIN SCAN input on the line 44 and to the signal CALIBRATE input on the line 76 to generate the various control signals used in the product characteristic signal normalizing network shown in FIG. 3. The CALIBRATE signal on the line 76 is connected to the clock input of a D-flip-flop 210. The D input of the flip-flop 210 is normally held to a logic high state. The Q output of the flip-flop 210 is applied to the D input of a second clocked D-flip-flop 212. Devices sold by Texas Instruments, Inc. under model number 74LS74 may be used as the flip-flops 210 and 212. The second flip-flop 212 is clocked by the BEGIN SCAN signal applied to the network 102 on the line 44. The Q and Q-NOT outputs of the flip-flop 212 provide the control signals CALIBRATE GATE and CALIBRATE GATE-NOT, respectively. The CALIBRATE GATE signal is applied on a line 214 to a reset gate 216.

The generation of the AUTOCAL GATE and PRODUCT GATE signals can be effected as follows: The BEGIN SCAN signal is also applied over lines 218, 220 and 222 to down-counters 224, 226 and 228, respectively. Each of the counters is clocked by a signal derived from a clock network 230 over lines 232A, 232B and 232C. The output of the clock network 230 is applied as the CLOCK signal for use in the product normalizing network. The counter 228, when enabled by the BEGIN SCAN signal applied over the line 222, counts down from a predetermined preset count. The signal generated when the count reaches zero triggers a one-shot 234, generating the AUTOCAL GATE signal. This signal may be inverted by the inverter 236 to produce AUTOCAL GATE-NOT. The down counter 226, after enablement by the BEGIN SCAN signal on the line 220, counts down to zero and triggers a one-shot 238 to generate the signal PRODUCT GATE. The counter 224 when enabled by the BEGIN SCAN signal counts down to zero to produce an END SCAN signal. Suitable for use as the counters 224, 226 and 228 are devices manufactured by Texas Instruments, Inc. and sold under model number SN74LS191 while the one-shots are implemented by devices sold by the same manufacturer under model number SN74LS221. Of course, any suitable alternate network, including a microprocessor operating under the control of a program, may be utilized to generate the signals AUTOCAL GATE, PRODUCT GATE and END SCAN.

The END SCAN signal is applied by a line 240 to the NAND gate 216. The occurrence and duration of the signals produced by the control network 102 is synchronized with the speed of the beam 22, as determined by the angular speed w of the mirrors 18. The output of the gate 216 on the line 242 resets the flip-flops 210 and 212. As is discussed herein, the generation of the signals AUTOCAL GATE and PRODUCT GATE is synchronized with the passage of the scanning beam 22 across the scan path 26. The signal AUTOCAL GATE is arranged to lie within the AUTOCAL signal pulse 78 generated by the beam 22 as it scans through the segment 26B (FIG. 1) and enters the aperture 40 in autocalibration filter assembly 38. Similarly, the signal PRODUCT GATE is arranged to have a duration which lies within the product web voltage signal 80 produced when the beam 22 passes through the segment 26D of its scan path (FIG. 1).

The operation of the product characteristic signal normalizing network 70 shown in FIGS. 2 and 3 may now be discussed. As noted earlier during any scan i the composite signal $v_i(x(t))$ output from the preamplifier 60 on the line 62 includes a first component 78 (AUTOCAL) which is a pulse representative of the passage of the beam 22 through the filter 38 as the beam moves in the segment 26B of the scan path 26. This pulse is representative of the reflectivity $R_{iF}$ of the particular mirror facet producing the scan. The second component 80, which is the web voltage pedestal signal, is generated when the beam passes through the segment 26D of the scan path and is representative of the portion of the product web under inspection during the i-th scan.

When it is desired to calibrate the system the operator depresses the calibration switch 75. This event generates the CALIBRATE signal on the line 76 to the control network 102 and results in the clocking of the first flip-flop 210 to place a logic high signal on the Q output pin thereof. The logic high signal at the Q output of the flip-flop 210 remains asserted until the flip-flop 210 is reset.

At the beginning of the next scan following the depression of the calibration switch 75 the sweep of the laser beam across the detector 42 generates the BEGIN SCAN signal which is applied on the line 44 to the control network 102. The occurrence of the BEGIN SCAN signal clocks the second flip-flop 212 and places a logic high signal (derived from the Q output of the first flip-flop 210) at the Q output thereof. The output from the flip-flop 212 is the CALIBRATE GATE signal and its complementary signal CALIBRATE GATE-NOT is derived from the Q-NOT output of the flip-flop 212. The CALIBRATE GATE signal is applied by the line 214 to the gate 216 but is not permitted to pass that gate until the occurrence of the END SCAN signal on the line 240.

The occurrence of the BEGIN SCAN signal also initiates a down count from the counters 224, 226 and 228. At a predetermined period of time synchronized with the speed of the scanning beam the output from the down counter 228 triggers the one-shot 234 to a logic high condition thus defining the AUTOCAL GATE signal. The complementary signal AUTOCAL GATE-NOT is generated by the inverter 236. The AUTOCAL GATE signal is arranged to lie within the AUTOCAL signal component 78 of the composite signal output from the preamplifier 60. The occurrence of the BEGIN SCAN signal initiates a down count from the second down counter 226. When the counter 226 down counts to zero, the one-shot 238 is triggered to generate the signal PRODUCT GATE. The PRODUCT GATE signal is asserted for a predetermined duration which lies within the web voltage signal component 80 of the composite signal from the preamplifier 60.

When the signal CALIBRATE GATE is asserted on the line 104 the switch 90 is opened, forcing any signal input to the normalizing network 70 on the line 62 to pass the low pass filter 106 before being applied by the line 96 to the ratioing analog-to-digital converter 98. The complementary signal CALIBRATE GATE-NOT is asserted on the line 126 closing the switch 124 and connecting the output of the sample and hold network 108 to the reference input of the ratioing analog-to-digital converter 98 through the automatic gain control network 114. During the calibration period (coextensive with the duration of the signal CALIBRATE GATE) the output on the line 138 from the multiplying digital-to-analog converter is held to zero due to the disablement of the memory control gate network 194 by the signal CALIBRATE GATE-NOT on the line 196. CALIBRATE GATE-NOT is also applied to the encode enable network 133 on the line 135, to the memory address control network 148 on the line 158 and to the memory write enable network 180 on the line 188.

At the occurrence of the AUTOCAL GATE signal the sample and hold network 108 is enabled on the line 110. As a result the magnitude of the AUTOCAL pulse 78 is sampled and held. The magnitude of the pulse signal 78 is representative of the reflectivity $R_{iF}$ of the particular mirror facet 18 utilized to generate the scan. After normalizing to a predetermined average value by the network 114, the sampled signal is applied to the reference input of the ratioing analog to digital converter 98.

The signals AUTOCAL GATE and AUTOCAL GATE-NOT are respectively applied on lines 154 and 156 to the memory address control network 148. As a result of the logic network therein provided, during the calibration period, a CLEAR signal is asserted on the line 174 to clear the counters 160 and 162. The counter 164 is cleared by the AUTOCAL GATE-NOT signal on the line 178. At the occurrence of the next positive-going transition of the CLOCK signal following AUTOCAL GATE-NOT the counters 160, 162 and 164 increment the address lines 150 to the memory 146. The succeeding negative-going transition of the CLOCK signal asserts the WRITE signal to the memory 146 from the memory write enable network 184 on the line 182.

The occurrence of the PRODUCT GATE signal on the line 139 to the encode enable network 133, together with the CALIBRATE GATE-NOT signal on the line 135 and the CLOCK signal on the line 137, results in the generation of ENCODE signals on the line 131 to the ratioing analog-to-digital converter 98. The ENCODE signal is generated on the positive-going transition of each CLOCK pulse. Thus, on each positive-going CLOCK signal during the PRODUCT GATE signal, the magnitude of the web voltage signal present at the input terminal of the converter 98 (representative of the signal generated by the product web 30 during that point in time within the scan segment 26D) is converted to a digital signal representative of the voltage input compensated for the reflectivity of the mirror facet 18 utilized during that scan. Mathematically, at each clock time during the PRODUCT GATE signal, the digital output from the converter 98 is represented as $$P_c(x(t)) = \frac{P_o(x(t)) \cdot R_{iF} \cdot E_o(x)}{R_{iF}} \quad (3)$$

where $P_c(x(t))$ is the product characteristic calibration signal generated from the point x on the web at the time t after compensation by the reflectivity of the mirror facet 18 used in that scan, $P_o(x(t))$ is the uncompensated product characteristic signal derived from the photomultiplier tube 54 as the result of the impingement of the beam 22 on the web at some point x across the web, at a time t, $R_{iF}$ is the reflectivity of the particular the mirror facet generating the beam 22 during the calibration scan, and $E_o(x)$ is the optical efficiency of the collecting arrangement for light entering at the point x measured in the direction of scan 24 within the segment 26D.

Of course, in Equation (3) the mirror reflectivity terms cancel, leaving the product characteristic calibration $P_c(x(t))$ signal independent thereof.

The addressing of the memory 146 occurs simultaneously with the encoding of the analog input to the converter 98. The address signals and data signals are allowed time to settle. The digitized input to the memory 146 is written into the addressed location at the falling edge of the CLOCK signal.

Therefore, at the end of the signal PRODUCT GATE during the calibration period the memory has stored therein a digitized representation of the product characteristic calibration signal $P_c(x(t))$ representative of the voltage output produced by a scan across an acceptable product, as compensated by the reflectivity $R_{iF}$ of the mirror used during the calibration scan. Mathematically, $$P_c(x(t)) = P_o(x(t)) \cdot E_o(x) \qquad (4)$$

This calibration signal is representative of the characteristic of an acceptable product upon which product signal normalization for subsequent analytical scans is based.

At the end of the scan 26 the END SCAN signal from the counter 224 resets the flip-flops 210 and 212 in anticipation of subsequent scans.

During each subsequent analytical scan, as, for example, the i-th scan (FIG. 4) the signal CALIBRATE GATE is not asserted, thus the switch 90 is left normally closed and the switch 124 is left normally open. The memory output gates 194 are enabled and the memory write terminal disabled.

At the occurrence of the AUTOCAL GATE during each subsequent analytical scan (e.g., the i-th scan) the sample and hold network 108 is enabled and the sampled magnitude of the AUTOCAL signal 78, representative of the reflectivity of the particular mirror facet used during that particular scan, is applied to the reference input of the multiplying digital-to-analog converter 136.

It should be recalled that during the calibration period the web voltage signal passes the low pass filter 106. As a result, the waveform applied to the input terminal of the ratioing analog-to-digital converter 98 is phase shifted by a predetermined time difference Delta-T (FIG. 4). The data converted by the converter 98 during the interval Delta-T at the beginning of the PRODUCT GATE signal is therefore not meaningful. To avoid the recall of this information, at the occurrence of the AUTOCAL GATE during subsequent analytical scans, the LOAD (FIG. 4) signal is generated and applied on the line 176 to the counters 160 and 162 (FIG. 3C). This results in the loading of a preset jumpered address signal to the memory 146 corresponding to the address at the time T during the calibration scan. Thus, only the meaningful portion of the stored product characteristic calibration signal $P_c(x(t))$ generated as a result of the passage of the beam 22 over the product is recalled from the memory 146.

The output from the multiplying digital-to-analog converter 136 is a signal representative of the calibration signal $P_c(x(t))$ as defined by Equation (4) scaled by the signal representative of the reflectivity $R_{mF}$ of the k-th mirror facet used in the particular subsequent scan. Mathematically, the reference signal applied to the ratioing analog-to-digital converter may be represented as $$V_{ref} = R_{mF} \cdot P_c(x(t)) \qquad (5)$$

The web voltage signal generated during the segment 26D of the i-th scan is applied to the to the $V_{IN}$ terminal of the converter 98. The digitized converter output during the i-th scan may be expressed as $$V_{out} = \frac{1}{R_{mF}} \cdot \frac{1}{P_c(x(t))} \cdot R_{mF} \cdot P_i(x(t)) \cdot E_o(x) = P_n(x(t)) \qquad (6)$$

Recalling from Equation (3) that the product characteristic calibration signal $P_c(x(t))$ equals the optical efficiency $E_o(x)$ multiplied by the uncompensated product classification characteristic signal $P_o(x(t))$, the reflectivity terms $R_{mF}$ of the particular mirror facet used in the i-th scan and the optical efficiency terms $E_o(x)$ both cancel, leaving the output signal $V_{out}$ from the converter 98 as a signal compensated for the reflectivity of the mirror facet used during that scan, and normalized by the product characteristic derived from acceptable product. This is the normalized product characteristic signal $P_n(x(t))$.

The output of the converter 98 is applied on the bus 202 to the digital-to-analog converter 200. The analog output signal, after amplification, is applied to the output line 72 for further processing.

As a result, the normalized product characteristic signal $P_n(x(t))$ generated from the network 70 and output on the line 72 in accordance with this invention is compensated for variations caused by differences in mirror reflectivity among mirror facets and is normalized to a signal representative of acceptable product to eliminate the effects of the nonuniform optical efficiency of the collecting arrangement.

Those skilled in the art, having the benefit of the teachings hereinabove set forth, may effect modifications thereto. These modifications are to be construed as encompassed within the scope of the instant invention, as defined by the appended claims.

What is claimed is:

1. In a product inspection system of the type having
    a rotating multifaceted mirror adapted to direct a beam of radiation in a scan traversing the product to be inspected, each facet having a reflectivity characteristic associated therewith,
    means operative during a predetermined portion of each scan for generating an electrical signal representative of the reflectivity characteristic of the mirror facet utilized during the scan,
    a radiation collecting arrangement positioned with respect to the product being inspected for generating an electrical signal representative of a predetermined physical property thereof, the collection arrangement having an optical efficiency associated therewith,
wherein the improvement comprises:
    a nonlogarithmic analog-to-digital converter responsive to the signal representative of the mirror reflectivity and to the signal representative of the product being inspected for generating a product signal that is independent of the reflectivity of the mirror facet utilized during the scan;
    the converter being adapted to generate during a calibration scan a calibration signal representative of an acceptable product, the calibration signal having a component representative of the optical efficiency of the radiation collecting arrangement; and
    means operative during a subsequent analytical scan for scaling the calibration signal by a signal representative of the reflectivity of the mirror facet used during that subsequent scan and for applying the scaled calibration signal to the converter thereby to generate a product signal that is both independent of reflectivity of the mirror facet used during the analytical scan and normalized to account for the efficiency of the collecting arrangement.

2. The product inspection system of claim 1 wherein the improvement further comprises:
   a network for sampling, during the predetermined portion of each scan, the electrical signal representative of the mirror reflectivity characteristic and for applying the same to the converter.

3. The product inspection system of claim 1 wherein the nonlogarithmic analog-to-digital converter is a ratioing analog-to-digital converter.

4. In a product inspection system of the type having
   a rotating multifaceted mirror adapted to direct a beam of radiation in a scan traversing the product to be inspected, each facet having a reflectivity characteristic associated therewith,
   means operative during a predetermined portion of each scan for generating an electrical signal representative of the reflectivity characteristic of the mirror facet utilized during that scan,
   a radiation collecting arrangement having an effeciency associated therewith positioned with respect to the product being inspected for generating an electrical signal representative of a predetermined physical property of the product,
wherein the improvement comprises:
   a nonlogarithmic analog-to-digital converter responsive to the electrical signal representative of the mirror reflectivity and to the signal representative of the product being inspected for generating during a calibration scan across an acceptable product a digitized calibration signal representative of an acceptable product, the calibration scan having a component that is representative of the efficiency of the collecting arrangement, the calibration signal being independent of the reflectivity of the facet utilized during the calibration scan;
   a memory for storing the calibration signal generated during the calibration scan and recalling the same during a subsequent analytical scan; and,
   means operative during a subsequent analytical scan for scaling the recalled calibration signal by a signal representative of the reflectivity of the facet used during that subsequent analytical scan and for applying the scaled calibration signal to the ratioing analog-to-digital converter to generate a product signal that is both independent of the reflectivity of the facet utilized during that analytical scan and normalized to account for the efficiency of the collecting arrangement.

5. The product inspection system of claim 3 wherein the improvement further comprises:
   a sample and hold network for sampling, during the predetermined portion of each scan, the electrical signal representative of the mirror reflectivity and for holding the sampled signal for the remainder of each scan; and
   a switch operable during a portion of the remainder of the calibration scan to apply the sampled signal to the ratioing analog-to-digital converter and during a portion of the remainder of the subsequent scan to apply the sampled signal to the scaling means.

6. The product inspection system of claims 3 or 4 wherein the improvement further comprises:
   a filter operable during the calibration scan for filtering the signal from the radiation collecting arrangement, the filter imparting a predetermined phase shift to the signal converted by the ratioing analog-to-digital converter and stored by memory during the calibration scan; and
   a memory address advance network operable during the subsequent analytical scan to advance the memory address location from which the calibration signal is recalled during the subsequent analytical scan to compensate for the phase shift imparted by the filter during the calibration scan.

7. The product inspection system of claim 3 wherein the nonlogarithmic analog-to-digital converter is a ratioing analog-to-digital converter.

8. A method of inspecting product using an optical radiation collection arrangement comprising the steps of:
   (a) directing a beam of radiation from one facet of a multifaceted mirror in a calibration scan over an acceptable product;
   (b) generating from the calibration scan an electrical caliration signal representative of acceptable product that has a component related to the efficiency of the optical collection arrangement, the calibration signal being independent of the reflectivity of the mirror facet used during the calibration scan;
   (c) storing the calibration signal for recall during a subsequent analytical scan across proudct to be inspected using a beam from a facet of the mirror;
   (d) scaling the recalled calibration signal during the analytical scan by a signal representative of the reflectivity of the mirror facet used during the subsequent scan; and,
   (e) applying the scaled calibration signal and a signal representative of the product scanned during the analytical scan to a analog-to-digital converter to directly generate a digitized proudct signal that is bth independent of the reflectivity of the facet used during the analytical scan and normalized to account for the efficiency of the collection arrangement.

9. In a product inspection system of the type having
   a rotating multifaceted mirror adapted to direct a beam of radiation in a scan traversing the proudct to be inspected, each facet having a reflectivity characteristic associated therewith,
   means operative during a predetermined portion of each scan for generating an electrical signal representative of the reflectivity characteristic of the mirror facet utilized during that scan,
   a radiation collecting arrangement positioned with respect to the product being inspected for generating an electrical signal representative of a predetermined physical property thereof, the collection arrangement having an optical efficiency associated therewith,
wherein the improvement comprises:
   (1) nonlogarithmic rationing means responsive during a calibration scan to the signal representative of mirror reflectivity and to the signal representative of acceptable product $P_o$ for generating a product calibration signal being exclusively representative of both acceptable product and the optical efficiency of the collecting arrangement and, during subsequent analytical scans, reponsive to a mirror-reflectivity scaled calibration signal and the product inspection signal $P_i$ generated during each analytical scan for generating a normalized product signal $P_n$ where $$P_n = P_i/P_o$$

and where $P_n$ is independent of both the optical efficiency and mirror facet reflectivity;

(2) a memory coupled to the output of the ratioing means for storing the product calibration signal generated during the calibration scan and for making the product calibration signal available during subsequent analytical scans; and (3) scaling means with its inputs connected to the memory and to the signal representing the mirror reflectivitY during each analytical scan and at its output to the ratioing means for generating the mirror-reflectivity scaled calibration signal used by the ratioing means to generate the normalized product signal $P_n$.

10. The product inspection system of claim 9 wherein the improvement further comprises:

a sample-and-hold automatic gain control network for sampling during a predetermined portion of each scan the electrical signal representative of the mirror reflectivity characteristic and for applying the same to the ratioing means during the calibration scan or to the scaling means during subseguent analytical scans.

11. The product inspection system of claim 10 wherein the scaling means is a multiplying digital-to-analog converter.

12. The product inspection system of claim 10 wherein the nonlogarithmic ratioing means is a ratioing analog-to-digital converter.

13. The product inspection system of claim 9 wherien the scaling means is a multiplying digital-to-analog converter.

14. The product inspection system of claim 13 wherein the nonlogarithmic ratioing means is a rationing analog-to-digital converter.

15. The product inspection system of claim 9 wherein the nonlogarithmic ratioing means is a rationing analog-to-digital converter.

* * * * *